(12) United States Patent
Schaller

(10) Patent No.: US 6,254,947 B1
(45) Date of Patent: *Jul. 3, 2001

(54) FLEXIBLE PLASTIC ARTICLES BEARING POLYMERIC SLIP COATINGS AND HAVING RAISED/RECESSED ROUGHNESS ON THEIR SURFACES

(75) Inventor: Raimund Schaller, Wimpassing (AT)

(73) Assignee: Semperit Aktiengesellschaft Holding, Vienna (AT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/927,285

(22) Filed: Sep. 11, 1997

(30) Foreign Application Priority Data

Sep. 12, 1996 (AT) .................................................. 1620/96

(51) Int. Cl.⁷ .......................... A61B 19/04; B32B 1/04; B32B 5/14; B32B 5/18
(52) U.S. Cl. ........................ 428/36.8; 2/161.7; 2/161.8; 2/168; 428/35.7; 428/138; 428/156; 428/159; 428/161; 428/165; 428/216; 428/220
(58) Field of Search .................. 428/35.7, 36.8, 428/156, 161, 165, 138, 159, 216, 220; 525/100, 101; 2/161.7, 161.8, 168

(56) References Cited

U.S. PATENT DOCUMENTS

| | | |
|---|---|---|
| 2,525,272 | 10/1950 | Rhoton .................................. 18/58.6 |
| 2,950,504 | 8/1960 | Suzuki ..................................... 18/58 |
| 3,098,755 * | 7/1963 | Barth et al. ............................. 117/33 |
| 3,411,982 | 11/1968 | Kavalir et al. ........................ 161/242 |
| 3,689,613 | 9/1972 | Talalay ..................................... 264/83 |
| 3,813,695 * | 6/1974 | Podell, Jr. et al. ....................... 2/168 |
| 3,813,696 * | 6/1974 | Podell et al. .............................. 2/168 |
| 4,061,709 | 12/1977 | Miller et al. ........................... 264/293 |
| 4,070,713 | 1/1978 | Stockum ................................... 2/168 |
| 4,082,862 | 4/1978 | Esemplare et al. ................... 427/133 |
| 4,084,265 | 4/1978 | Anfelt . |
| 4,100,309 | 7/1978 | Micklus et al. ........................... 427/2 |
| 4,143,109 * | 3/1979 | Stockum ............................... 264/112 |
| 4,310,928 | 1/1982 | Joung ................................... 0/161 R |
| 4,482,577 | 11/1984 | Goldstein et al. ........................ 427/2 |
| 4,499,154 | 2/1985 | James et al. ........................... 428/494 |
| 4,540,407 | 9/1985 | Dunn ..................................... 604/292 |

(List continued on next page.)

FOREIGN PATENT DOCUMENTS

| | | |
|---|---|---|
| 132778 | 4/1900 | (DE) . |
| 2628059 | 1/1977 | (DE) . |
| 0543657 | 5/1993 | (EP) . |
| 0681912 | 11/1995 | (EP) . |
| 9213497 | 8/1992 | (WO) . |
| WO 92/13497 * | 8/1992 | (WO) ............................ A61B/19/04 |
| 93/06996 | 4/1993 | (WO) . |
| WO 93/06996 * | 4/1993 | (WO) ............................ B32B/25/04 |
| 95/17107 | 6/1995 | (WO) . |

Primary Examiner—Rena L. Dye
Assistant Examiner—Sandra M. Nolan
(74) Attorney, Agent, or Firm—Greenblum & Bernstein, P.L.C.

(57) ABSTRACT

The invention relates to an article, in particular a glove, a condom, or the like, which is comprised of a flexible rubber and/or plastic, is embodied having at least one section of the surface intended contact or rest against human skin, which article is provided with a slip coating in a section of the surface. This slip coating is comprised of a polymeric material and at least in sections, has repeating shape deviations of the surface that are recessed in relation to a raised, net-like structure. The ratio of the average spacings between the shape deviations to their depth in relation to the raised, net-like structure is between 500:1 and 5:1 and the average roughness depth is between 0.5 and 100 $\mu$m, preferably between 1 and 40 $\mu$m.

46 Claims, 5 Drawing Sheets

U.S. PATENT DOCUMENTS

| | | | |
|---|---|---|---|
| 4,851,266 | 7/1989 | Momose et al. | 427/353 |
| 4,853,978 | 8/1989 | Stockum | 2/167 |
| 5,014,362 | 5/1991 | Tillotson et al. | 2/168 |
| 5,069,965 * | 12/1991 | Esemplare | 428/330 |
| 5,088,125 | 2/1992 | Ansell et al. | 2/167 |
| 5,138,719 | 8/1992 | Orlianges et al. | 2/168 |
| 5,272,771 * | 12/1993 | Ansell et al. | 2/167 |
| 5,284,607 * | 2/1994 | Chen | 264/37 |
| 5,742,943 * | 4/1998 | Chen | 2/168 |
| 5,881,386 * | 3/1999 | Horwege et al. | 2/161.7 |

* cited by examiner

FLEXIBLE PLASTIC ARTICLES BEARING POLYMERIC SLIP COATINGS AND HAVING RAISED/RECESSED ROUGHNESS ON THEIR SURFACES

CROSS-REFERENCE TO RELATED APPLICATION

The present application claims priority under 35 U.S.C. § 119 of Austrian Patent Application No. 1620/96 filed Sep. 12, 1996, the disclosure of which is expressly incorporated by reference herein in its entirety.

BACKGROUND OF THE INVENTION

Field of the Invention

The invention describes an article made of a flexible rubber and/or plastic as well as a process for making this article.

Many flexible articles that are untreated on the surface, particularly those made of plastic and rubber, have a relatively high degree of friction resistance in relation to human skin. This is why untreated rubber gloves, for example, are almost impossible to put on. In order to make it easier to put these gloves on, glove powder (e.g. starch powder, talcum, etc.) is conventionally deposited as a parting compound on the inside of the glove. The use of powder, though, is particularly problematic in the medical field because residual powder can lead to granule formation if it gets into open wounds. Another important application field for powder-free products is the electronics industry.

A classic method for making articles of rubber and in particular, gloves that are slippery in relation to human skin without the use of powder, involves surface chlorination. In this connection, the article is treated with aqueous, chlorine gas-containing mediums and is then washed. Primarily, this produces a favorable slipperiness in relation to dry human skin, but this surface chlorination synthetically alters the polymer structure and thus produces a distinct diminishing of the physical and chemical properties of the article (strength, tear elasticity, water swelling, storability, etc.). However, surface-treated gloves of this kind are also usually difficult to put on with wet hands.

Coating with hydrogels represents an alternative surface treatment. Some hydrogels of this kind have been known for a long time. For example, these are polyurethane, polyvinylpyrrolidone, polyhydroxyethylacrylate or polyhydroxymethacrylate, polyhydroxypropylacrylate or polyhydroxypropylmethacrylate, and are copolymers with one another or with acrylic acid or methacrylic acid, acrylic ester or methacrylic ester, or vinylpyridine.

A coating of this kind has been disclosed by U.S. Pat. No. 3,813,695, which describes a dipped rubber glove that is coated on the inside with a hydrogel polymer such as polyvinylpyrrolidone, polyhydroxyethacrylate or polyhydroxymethacrylate, polyhydroxypropylacrylate or polyhydroxypropylmethacrylate, and copolymers of these with one another or with acrylic acid or methacrylic acid. The preferred hydrogel polymer is a copolymer of 2-hydroxyethylmethacrylate with methacrylic acid or with 2-ethylhexylacrylate or a ternary copolymer of 2-hydroxyethylmethacrylate, methacrylic acid and 2-ethylhexylacrylate.

A known manufacturing process is disclosed by U.S. Pat. No. 4,482,577. This patent discloses the coating of a flexible, vulcanized surgical glove with a hydrophilic polymer, by means of which the depositing of powder on the inside of the glove can be omitted. The copolymer used in this instance is comprised of a mixture of 2-hydroxyethylmethacrylate and 2-ethylhexylacrylate.

Another process according to U.S. Pat. No. 4,100,309 discloses the depositing of a slippery coating comprised of a polyurethane-polyvinylpyrrolidone complex. Normally with these products or processes, the hydropolymer is deposited on the product together with a hardener in dissolved form, then the solvent is removed by drying, wherein the polymer layer is hardened, thus forming a hydrogel coating.

Other known embodiments disclose the use of vinylidene halogenide lattices or vinyl halogenide lattices for producing a slip coating on rubber articles, e.g. U.S. Pat. No. 5,069,965, where the slippery quality is mostly achieved by means of polymers that contain chlorine.

DE 26 28 059-C and U.S. Pat. No. 4,082,862 disclose the use of diverse latex mixtures for producing a slip coating. In particular, mixtures comprised of at least two latex types are used in this connection, wherein a latex type with a high elasticity is used as a bonding agent and a latex type with a high degree of hardness or low elasticity is used to obtain a sufficient slipperiness. These recipes are usually more or less favorable compromises between slipperiness, sufficient film flexibility, and adhesion of the film to the rubber product. In particular, with the use of the slip coating in very flexible, highly elastic rubber articles, there are often problems in this connection to the effect that the slip coatings used either begin to detach from the foundation when stretched or do not have a satisfactory slipperiness in actual use.

In the process according to EP 0 681 912-A2, the slip coating is comprised of a copolymer latex, which is fixed to the carrier layer with the aid of a coagulation step. The latex is comprised of a copolymer that contains a significant portion of hydrophilic monomer components.

U.S. Pat. No. 4,143,109 describes another method for producing slipperiness in relation to skin with powder-free medical gloves made of natural latex. In this instance, bonded cornstarch particles or polyethylene particles are deposited in a carrier layer, wherein the carrier layer is thinner than the diameter of the particles and the particles protrude from the surface. The powder particles bonded in this manner produce a sufficient slipperiness of the glove interior. This embodiment for achieving slipperiness in relation to skin has problems when the product is stretched to a great degree, which is inevitable when putting on latex medical gloves: The surface-bonded particles detach easily and the powder-free nature is no longer assured.

All of the above-described powder-free articles can only be produced with satisfactory product properties only under the most precise adherence to the affiliated process requirements and material recipes. While a favorable slipperiness of the surfaces in relation to dry skin is usually achieved with ease, very often there are difficulties in the reproducibility with regard to wet slipperiness. In particular with thin-walled flexible articles, which must have favorable slipperiness even when stretched to a great degree, it often takes years of high-precision optimization on the part of the manufacturer, who usually has to adopt compromises with regard to diverse product properties. Despite the use of polymeric slip coating hydrogels, the surface is frequently lightly chlorinated. Other manufacturers, in spite of the polymer slip coatings, use additional small quantities of glove powder. Still other producers see themselves as confronted with constant fluctuations with regard to the wet slipperiness of their products.

SUMMARY OF THE INVENTION

The object of the current invention is to produce articles made of plastic and/or rubber, which have a favorable slipperiness in relation to human skin, particularly wet skin, and to develop a process which can be easily reproduced.

This is attained by an article made of a flexible rubber or plastic, such as a glove, a condom, or the like, which includes a surface section that contacts or rests against human skin, and which is provided with a slip coating in a section of the surface that is comprised of a polymeric material and has at least a partial area having repeating surface shape deviations that are recessed in relation to a raised, net-like structure, where the ratio of the average spacings between the shape deviations to their depth, in relation to the raised, net-like structure, is between 500:1 and 5:1 and the average roughness depth is between 0.5 and 100 $\mu$m, preferably between 1 and 40 $\mu$m. In this connection, it is advantageous that the flexible products with the raised net structure and the recessed faces and the slightly roughened surface constituted by this have a significantly better slipperiness than smooth slip coatings, primarily in relation to wet human skin. This is particularly true for wet slipperiness, which is often difficult to achieve. A further advantage of the current invention is that avoiding occlusive skin contact makes wearing the articles more comfortable, improves their ability to be taken off, and if necessary, significantly improves their absorption of sweat. It is also significant that as a result of the rigorous reduction of the contact area between skin and polymer, in many cases, a significantly improved skin compatibility can be expected. In addition, allergic reactions are reduced and there is no confined feeling after the product is put on. It is advantageous that the roughened surface morphology according to the invention can be produced without additional mechanical or chemical treatment, such as embossing or chlorinating processes, and can also be produced, for example without the addition of a parting compound, e.g. powder or silicone. As a result, a favorable slipperiness can also be achieved using less optimal slip coating polymers. When a roughened surface structure is maintained, a favorable slipperiness can be achieved in both the wet and dry states.

According to another aspect of the invention, the flexible article is characterized in that between 50 and 90%, preferably between 60 and 80%, of the partial area's repeating surface shape deviations are recessed. This is also advantageous since the wealth of micro-cavities formed in this manner can considerably reduce the friction potential or the contact area between the article and human skin.

According to another aspect of the invention, the flexible article is characterized in that at least 50% of the shape deviations, according to a top view of the slip coating, are encompassed on all sides by the net-like structure. This assures that a large part of the slip coating is kept at a distance from the skin by the net-like structure, even when the article is being worn, in which state the article is slightly stretched or drawn taut, so that in spite of the roughening, on the one hand, the user does not get the feeling that the article is chafing his skin and on the other hand, the movement of the hand, for example of the fingers, is not hindered since the slip coating or the partial surface of the slip coating does not stick to the wet skin.

The flexible article gives the skin a comfortable feeling if the slip coating comprises at least one natural and/or synthetic latex, or if the slip coating comprises a latex mixture and is fixed to the surface of the carrier layer.

Favorable properties for the slip coating and a firm adhesion of it to the carrier layer are achieved according to another aspect of the invention if the slip coating material comprises polyurethane.

A favorable skin compatibility for articles is achieved according to another aspect of the invention where the slip coating material comprises polyacrylates and/or polymethacrylates and/or polysiloxanes or other comparable products.

According to yet another aspect of the invention, surface roughness that is caused by the corresponding secondary treatment through chemical and/or physical reactions can be easily produced where the slip coating comprises 0 to 30 wt. % polyurethane, 1 to 40 wt. % polyacrylate, 1 to 20 wt. % polysiloxane, and 0 to 40 wt. % filler. Such surface roughness may be produced where the filler material comprises pulverized or powdered materials such as chalk, lime, cornstarch, silicon dioxide, and/or gypsum.

According to yet another aspect of the current invention, the use of a polymeric material in a slip coating that contains water absorbing groups makes the flexible articles particularly comfortable properties for people who perspire a lot.

According to still another aspect of the invention, perspiration retention on the surface of the skin can be better controlled in the region of the roughened surfaces in the sections, since the glove can absorb a higher quantity of moisture, where the polymeric material of the slip coating comprises intensely hydrophilic groups, for example acrylic acid and/or methacrylic acid and/or an acrylate and/or a methacrylate.

According to another aspect of the invention, a favorable connection with the slip coating in the sections can be achieved where the slip coating material has high surface adhesion and preferably is not cross-linked.

According to yet another aspect of the invention, the wet slipperiness of the articles can be additionally improved where silicone is deposited onto the regions of the slip coating which have surface roughening.

According to still another aspect of the invention, uniform slip behavior of the article is achieved where silicone is deposited onto regions of the slip coating.

According to yet another aspect of the invention, a very thin coating of silicone that increases slipperiness while at the same time preventing adhesion of the recesses, is achieved where the silicone on the surface sections of the slip coating is between 0.05 and 3 g/m$^2$, preferably 0.25 g/m$^2$.

According to another aspect of the invention, a slip coating or coatings is or are deposited on the inner surface of a sleeve-like carrier layer. According to yet another aspect of the invention, the slip coating is or are deposited on the outer surface of the sleeve-like carrier layer. According to still another aspect of the invention, the average roughness depth is lower in sections having lower relative movement between the flexible article and the skin of the user. These features provide slipperiness and slip properties as well as a roughness that corresponds, for example, to the grasping of tools or articles used in the assembly field.

According to another aspect of the invention, it is advantageous where at least one layer of the carrier layer is comprised of a latex product, which contains a polymer, e.g. a natural and/or synthetic latex since it can be used to produce extremely thin and extremely elastic articles that are also very resilient.

According to yet another aspect of the invention, the quality of the flexible articles can be considerably improved where the slip coating is provided on a carrier layer comprised of at least one layer, which preferably is slightly cross-linked. According to still another aspect of the invention, the latex of the carrier layer is pre-cross-linked.

According to yet another aspect of the invention, the article has a high degree of elasticity and suppleness where the carrier layer comprises an aqueous solution of a coagulant, which contains calcium nitrate, polyethylene glycol, a water soluble silicone or chalk, and a pre-cross-linked natural latex mixture.

According to another aspect of the invention, to make the carrier layer resistant the carrier layer contains a pre-cross-lined synthetic latex, e.g. chloroprene latex, NBR latex, X-NBR latex, or SBR latex.

According to yet another aspect of the invention, the carrier layer is embodied in a sleeve-like article having an outer surface and an inner surface which can be used to adapt the roughness of the individual surfaces or sections to the various intended uses of the article. According to another aspect of the invention, at least one surface section is disposed on the inner surface of the article, particularly of the glove, to achieve the intended roughness. Moreover, according to another aspect of the invention, at least one surface section is disposed on the outer surface of an article, particularly of a glove, which achieves the intended roughness.

According to another aspect of the invention, chlorinating the carrier layer on its surface further improves the effect of the roughness in the region of the carrier layer, or it produces at least a partial improvement of the slip properties in those regions where there is no roughening. Further, the raised edge regions of the chlorinated surface deformations caused by the chlorination may protrude above the neighboring surface zones by a height of 0.5 to 10 $\mu$m, preferably less than 1 $\mu$m.

According to another aspect of the invention, the inner surface of the slip coating of the article is provided with at least one of a coating of silicone and a treatment with chlorine, to cause preferred grading of the roughness and of the slipperiness of the flexible article in its various regions.

According to yet another aspect of the invention, the flexible article may be a rubber glove. According to yet another aspect of the invention, the article may be a medical glove.

Universal adaptations of adhesion, grip security, or slipperiness and wet slipperiness are achieved, according to another aspect of the invention, where the slip coating is deposited on the inner surface of the rubber glove or the medical glove. Further, only a section of the slip coating may have shape deviations in the region of its surface. Moreover, the surfaces of the rubber gloves or the medical gloves that are oriented toward the palm of the hand, or the back of the hand, may be provided with a slip coating, and if need be, at least sections of this slip coating may be provided with the surface shape deviations. Further, an outer surface of the rubber or latex glove may be provided with shape deviations where the ratio of the spacings of adjacent shape deviations to their depth is between 100:1 and 5:1, and their average roughness depth is between 0.5 and 100 $\mu$m, and preferably between 1 and 40 $\mu$m. Moreover, sections of the outer surface of the rubber glove or the medical gloves according to the invention may be provided with a slip coating and have surface shape deviations, at least in the region of the slip coating.

The invention also includes a process for manufacturing a flexible article, in particular a glove, where a carrier layer is made of plastic and/or rubber, and at least one section of its surface that has a slip coating, which is provided with a roughness in the region of its surface remote from the carrier layer. Moreover, where the slip coating is applied to the carrier layer by means of dipping and is dried immediately afterward, preferably for 10 to 600 sec. by means of hot air, and then the slip coating is treated with water at a temperature between 40 and 100° C., preferably between 60 and 80° C., or is rinsed with the hot water so that afterwards, the water content of the slip coating is reduced by approx. 40 to 70%, preferably 50 to 60%, such that a slip coating in a section of the surface is comprised of a polymeric material with at least a partial area having repeating surface shape deviations that are recessed in relation to a raised, net-like structure. The individual, succeeding measures produce a distortion in the surface of the slip coating and therefore produce the sinking of the recesses, which represent the deviations in shape, in relation to the intermediary pieces of the net-like structure that remain at the original height, by means of which a higher wearing comfort is produced by the higher elasticity, primarily when moving the fingers, and the slipperiness of the article is additionally improved in relation to human skin, above all when it is wet. Furthermore, the roughenings produced during the manufacturing process do not absolutely require additional treatment such as a subsequent chlorination or the application of a parting compound or the like.

According to another aspect of the invention, the flexible article is exposed to infrared radiation immediately following the draining period after the rinsing of the article with the hot water, and this permits the roughened structure that appears during the course of the drying process on the top side of the slip face or the net-like structure of intermediary pieces, which protrude by the measure of between 0.5 $\mu$m and 100 $\mu$m above the deviations in shape that are sunk with the dehydration, to produce a support grid that is supported on the surface of the skin and reduces the contact area between the skin and the article, without producing an uncomfortable scratchy effect that is felt when the surface is too rough.

The high temperature of the emitting body that gives off the infrared radiation, such as stove tiles, which may have temperatures of between 350° C. and 700° C., permits rapid stabilization of the surface deformations without causing the net-like structure to be reformed.

According to another aspect of the invention, by exposing the article to infrared radiation for between 1 and 5 minutes, the chemical reaction is finished in the entire article, both in the carrier layer and in the slip coating, and a secure connection is produced between these layers.

According to yet another aspect of the invention, the sunken shape deviations produced by the dehydration are prevented from leveling out again as a result of a uniform distribution of, for example, the gelatinous fluid over the coating before they are permanently fixed, where the draining period between the rinsing of the article with the hot water and the application of infrared radiation is between 10 and 180 seconds, preferably between 20 and 50 seconds. The flexible may also be subjected to hot air during the draining period.

A favorable adhesion between the carrier layer and the slip coating is achieved according to yet another aspect of the invention, when during the drying of the coagulation solution of the latex product and/or the slip coating, which is preferably carried out with hot air, the surface of the latex product and/or the slip coating is converted from a liquid state into the gelatinous or solid state. Such adhesion also may be achieved when the drying of the surface of the latex product and/or the slip coating is carried out at a temperature from 70 to 140° C., preferably at a temperature from 90 to 110° C. Further, the drying process of the latex product and the slip coating may take between 10 and 80 seconds, preferably between 15 and 60 seconds.

According to another aspect of the invention, rapid dehydration of the slip coating accompanied by a more pronounced sinking of the shape deviation in relation to the net-like structure is achieved where the temperature of the hot water for rinsing the slip coating is between 40 and 95° C., preferably between 70 and 90° C., and the treatment lasts for 15 sec. to 8 min., preferably 30 sec. to 4 min.

According to still another aspect of the invention, the use of a slip coating comprised of a dispersion containing at least one polymeric material, increases skin compatibility and simplifies the manufacture of shape deviations that are sunken in relation to the net-like structure.

According to another aspect of the invention, a composition of dispersion is comprised of a mixture containing 0 to 30 wt. % of a polyurethane dispersion, 1 to 40 wt. % of a polyacrylate dispersion, 1 to 20 wt. % of a polysiloxane dispersion, and 0 to 10 wt. % filler, and the remaining portion water, encourages the formation of the net-like structure and the recesses that constitute the shape deviations. Moreover, the filler may comprise powdered or pulverized materials such as chalk, lime, cornstarch, silicon dioxide, and/or gypsum. Further, the viscosity of the dispersion of the slip coating may be between 5 and 30 mPa.'s, preferably 7 to 11 mPa.'s.

According to still another aspect of the invention, the roughness is created by the form surfaces on the carrier layer, which can improve the production of roughness in the carrier layer and/or the slip coating or in sections of them. According to another aspect of the invention, the recesses are produced by the pressing-in of fine beads or by sandblasting can improve the roughness of the carrier layer and/or the slip coating, or in sections of them.

According to still another aspect of the invention, a slip coating, preferably comprising silicone, is deposited onto the roughened surfaces of the flexible article.

Finally, according to yet another aspect of the invention, the shape deviation of the outer surface of the glove, in particular of a rubber or latex glove, as a result of the depositing of the carrier material onto a form whose surface has shape deviations in which the ratio of the spacings of adjacent shape deviations to their depth is between 100: 1 and 5:1, and the average roughness depth is between 0.5 and 100 µm, preferably between 1 and 40 µm, improves the handling of tools or machine parts or components, particularly if these gloves are used in the assembly of electronic components or clean room parts.

BRIEF DESCRIPTION OF THE DRAWINGS

The invention is explained in detail below in conjunction with exemplary embodiments shown in the drawings.

DETAILED DESCRIPTION OF THE INVENTION

Figure 1:
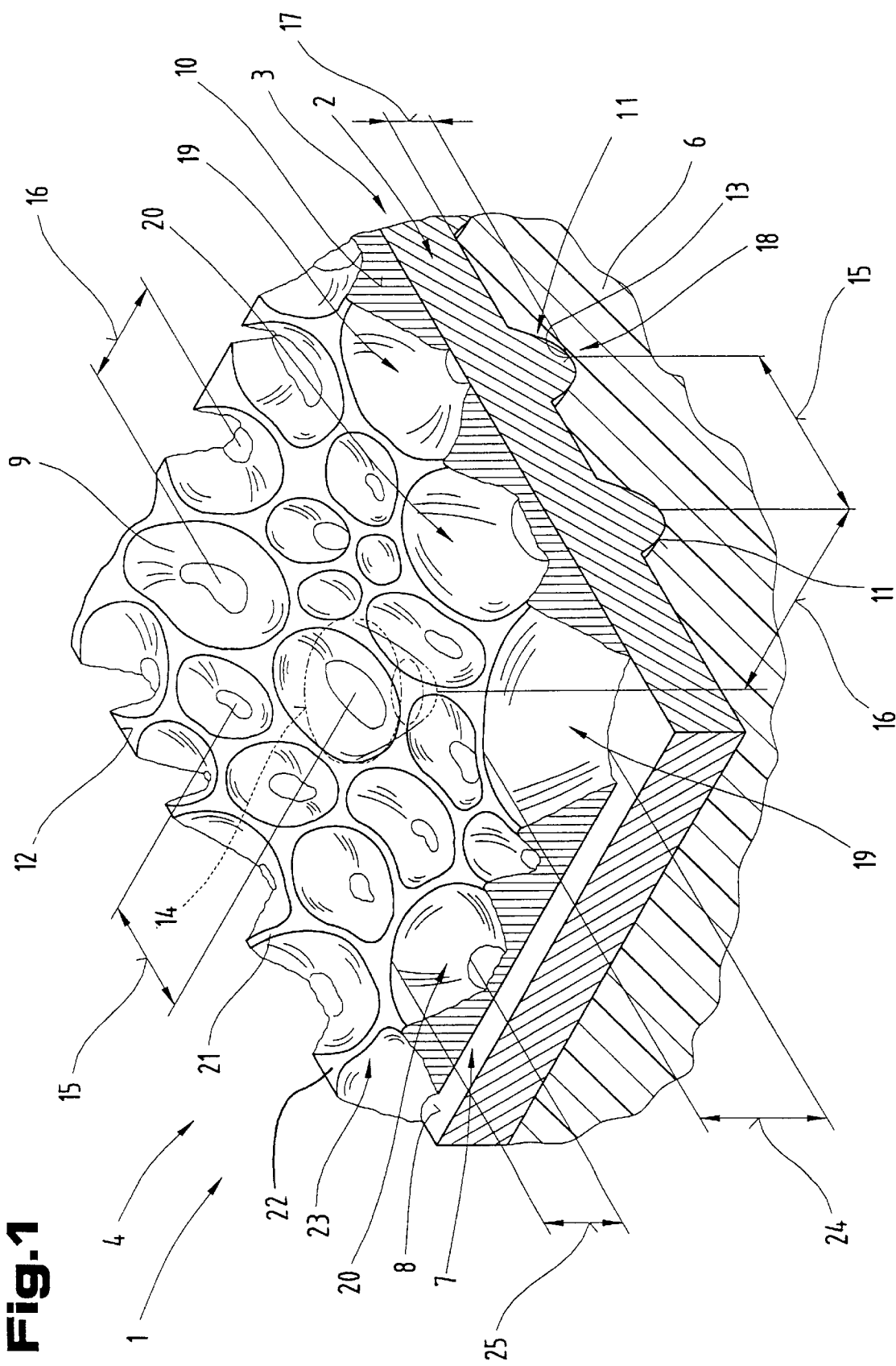
FIG. 1 is a sectional, simplified schematic diagram of a part of an article according to the invention, with a slip face and a corresponding roughness.

By way of introduction, it should be emphasized that in the different exemplary embodiments described, identical parts are provided with the same reference numerals or the same component labels, wherein the disclosures contained in the entire specification can by analogy be transferred to identical parts with the same reference numerals or the same component labels. Furthermore, individual features from the different exemplary embodiments shown can also represent embodiments according to the invention that are independent in and of themselves.

FIG. 1 shows a flexible article 1 according to the invention, which is preferably embodied as a latex product 2. This product is comprised of a carrier layer 3, which, as is usually the case in the manufacture of thin-walled rubber and plastic articles, is preferably formed by means of a multiple dipping process. These articles 1 can be gloves 4, for example medical, surgical, and experimental gloves, catheters, condoms, finger cots, bathing caps, swim fins, or protective gloves for work in clean room areas. Thin-walled articles, in particular elastic articles made of rubber and/or plastic such as the glove 4, for example, are preferably obtained by dipping a form into a latex product 2, wherein this latex product 2 can be based on natural latex and on synthetic latex. The latex products 2 used may or may not be in a cross-linked state. In the case of a latex product 2 that is not cross-linked or is only partially cross-linked, the rubber layer produced has to be additionally vulcanized on the dipping form, by means of which a carrier layer 3 is constituted.

Preferably a latex product 2 is used which contains at least one polymer 5 that is cross-linked or is cross-linked to a large degree. This latex product 2 is deposited and coagulated on a dipping form 6, which predetermines the shape of the final product, and thus produces a thin layer, namely the carrier layer 3 comprised of an elastic, relatively resistant rubber material. The latex product 2 contains the usual compounding admixtures such as sulfur, zinc oxide, organic accelerators (among others, zinc salts of dithiocarbamates, thiurams, thiourea, etc.), stabilizers, waxes, anti-aging substances, viscosity regulators, fillers, colors, etc. Natural caoutchouc and synthetic caoutchouc, which is suitable for use in dipping processes, can be used as the latex product 2 for the carrier layer 3. Out of the natural and synthetic lattices, preferably natural caoutchouc, polychloroprene, synthetic polyisoprene, nitrile-butadiene caoutchouc and stirene-butadiene caoutchouc, or a mixture of these polymers can be used.

Naturally, all other manufacturing processes, which are known to one skilled in the art from the prior art, can be used for the carrier layer 3.

It has long been known in the trade that in order to be able to manufacture reproducible layers out of latex products on a form, a coagulant is deposited on the form, for example a ceramic form provided with corresponding roughenings. At the same time, the form is usually dipped into a basin or a container which contains the coagulant in fluid form. This coagulant can have any composition known from the prior art, for example alcohol solutions of calcium salts or the like. The coagulant also contains a parting compound such as talcum or calcium carbonate which, if it is acid-soluble, can be leached from the surface layers with subsequent acid treatments so that a powder-free glove is produced. The coagulant is then dried.

Then, the form with the preferably dried coagulant is dipped into a container in which the latex product 2 is kept on hand as a dispersion or fluid so that an average layer thickness of 100 $\mu$m to 300 $\mu$m is achieved. Preferably, it is also possible to dip the form into the latex product 2 several times in order to increase the layer thickness, where in the mean time, a short drying of the latex layer can take place.

Because of the chemical reaction of the latex product 2 with the coagulant, the latex product 2 deposited in fluid form hardens. Preferably, immediately after the depositing of the latex product 2 on the form, it is dried for a short time with hot air so that the surface of the carrier layer 3 hardens or gels, wherein this is dried for 15 to 60 sec., for example in a heating furnace or a container through which warm air that is conveyed at a temperature between 70° C. and 140° C. is conveyed through.

After this intermediary drying, and in the course of the above-outlined dipping process, a slip coating or layer 9 made of polymeric material 10 is deposited on the dried carrier layer 3 at least in a section 7 of a top side 8 of the carrier layer 3 by means of dipping or spraying in one or more steps. The layer thickness of this slip layer 9 can be established in accordance with the various requirements, in particular the subsequently desired roughness depth and is between 2 $\mu$m and 80 $\mu$m, preferably from 2 $\mu$m to 30 $\mu$m.

This slip coating 9 can be comprised of a mixture of a number of polymeric materials 10 such as an aqueous polyurethane dispersion. Depending on the intended use, a polyacrylate, a polysiloxane, a polymethacrylate, a carboxylated stirene-butadiene copolymer, a polyvinylpyrrolidone, a cationic polyurethane, for example with a molecular weight of at least 100,000, can be used just like the nonionic or anionic embodiments of these above-mentioned materials. These aqueous dispersions and arbitrary mixtures of them form layers or films with favorable basic mechanical properties and have elastic properties similar to those of the carrier layer 3. Naturally, this slip coating 9 can also be comprised of a mixture of several different polymeric materials 10 in an aqueous dispersion. In this manner, the dispersion is preferably comprised of a mixture of 0 to 30 wt. % of a polyurethane dispersion, 1 to 40 wt. % of a polyacrylate dispersion, 1 to 20 wt. % of a polysiloxane dispersion, and 0 to 10 wt. % fillers, and the remaining portion can be comprised of water. Powdered or pulverized materials such as chalk, lime, gypsum, silicon dioxide, and/or cornstarch can be used as fillers. However, other mixtures can also be used for producing the slip coating 9 in the article 1 according to the invention or in the glove 4, for example 5 to 15 wt. % of a polyurethane dispersion, 1 to 8 wt. % of a polyacrylate dispersion, 2 to 6 wt. % of a polysiloxane dispersion, and 4 to 6 wt. % fillers, and the remaining portion can be comprised of water, just as the mixture ratios indicated below in the individual parentheses, in which ratios the individual contents in wt. % of the dispersions of polyurethane, polyacrylate, polysiloxane, and fillers are divided by diagonal slashes, wherein the remaining portion is brought to 100 wt. % by the addition of water. The dry content of the dispersions can be determined by one skilled in the art, wherein the solids content can be between 30 and 50% polyurethane, between 30 and 50% polyacrylate, and between 20 and 40% polysiloxane. Mixtures according to the present invention can include the following weight ratios of polyurethane/polyacrylate/polysiloxane/filler: (2-7/4-10/3-12/0-5), (0-10/2-6/3-10/3-7), (8-18/5-15/4-7/5-10), (12-22/12-26/16-20/0-4), (17-26/18-32/10-14/2-6), (24-30/28-40/15-20/6-9), (24-30/25-35/5-10/3-7), (21-27/4-9/1-4/6-8), (21-27/12-22/3-9/4-7), (21-27/28-36/12-20/2-7), (9-12/1-3/2-6/5-9), (12-22/4-9/1-4/0-3), (17-26/5-11/7-10/0-4), (2-7/12-22/14-20/3-8), (5-15/28-36/14-20/5-10), (0-10/24-29/9-16/5-8).

In the particular instance of manufacturing dipped articles as in the case of the article 1, its surface is usually subdivided into the dipping form side and the dipping bath side. In the current exemplary embodiment, the dipping form side is called the underside 11 and rests against the dipping form 6, which can be comprised for example of porcelain, plastic, or the like.

The dipping bath side is constituted by either the top side 8 of the carrier layer 3 or the surface 12 of the slip coating 9. In the current instance, a surface 13 of the dipping form 6 is preferably provided with regularly repeating shape deviations 14. These are comprised by shape deviations 14, for example recesses in the surface 13, or by means of raised areas that protrude above the surface 13. A ratio of spacings 15, 16 to their depth 17 is between 100:1 and 5:1. As a result, the roughness of the underside 11 of the article 1 corresponds to the morphology of the dipping form 6. The depth comes to between 0.5 and 100 $\mu$m, preferably between 1 and 40 $\mu$m.

Because of the slight depth 17 of the shape deviations 14, it should be expressly emphasized at this point that in all depictions, for the sake of improved schematic representation of the roughness depth, these shape deviations are shown completely out of proportion and greatly enlarged in order to be able to represent and explain the functions and also the disposition of these shape deviations 14 and the other shape deviations as well.

As explained in more detail below, if it is assured that a layer thickness of the carrier layer 3 as well as of the slip coating 9 deposited on this is maintained in sections 7 over a large part of the article 1, then a corresponding roughness is also embodied on the surface 12 of the slip layer 9 oriented toward the dipping bath side. This dipping bath side usually forms the inside of the product when it concerns, for example, sleeve-shaped articles 1 or thin-walled rubber products since when the articles 1 are pulled from the dipping form 6, the products are turned inside out. Normally, the surface 12 of the side of the article 1 that comes into contact with the skin of the user and that should be correspondingly embodied in order to prevent skin irritations or to permit the secretion of sweat without irritating the skin. With the current article 1, it is provided that either the dipping form side or the dipping bath side or both can be equipped with a corresponding roughness. Accordingly, it is also possible that a slip coating 9 can be disposed in sections 7, 18 on one or both sides, but can of course also be disposed over the entire top side 8 or underside 11.

Within the scope of the current invention, though, it is also possible that a slip coating 9 is disposed on both the top side 8 and the underside 11, wherein this can be carried out by virtue of the fact that after production of the carrier layer 3, the article 1 is pulled off the dipping form 6 and put back on the same dipping form or on a different one inside-out, that is with the top side 8 resting against the dipping form 6, in order to then likewise deposit a slip coating 9 onto the underside 11 as well, which is now disposed on the dipping bath side.

By means of shape deviations 19, 20 in the slip coating 9, which are disposed at least in sections 7 on the top side 8 of the carrier layer 3, perspiration retention can be regulated and wearing comfort can be increased.

The contact area between the skin and the slip coating 9 or the polymeric material 10 should be kept as low as possible in order to prevent adhesion to human skin, which is wet for example, by means of which among other things, the danger of skin irritations and possibly allergic reactions is minimized. Furthermore, by means of the surface 12 embodied according to the invention, a favorable slipperiness of the flexible articles 1 in relation to human skin and as a result, a favorable ability to be put on when wet or dry is achieved.

Furthermore, it can clearly be inferred from the depiction in FIG. 1 that in relation to the shape deviations 14 in the region of the underside 11 of the carrier layer 3, different shape deviations 19, 20 are simultaneously disposed in the surface 12 of the slip coating 9. These shape deviations 19, 20 are disposed between intermediary pieces 21, 22 of a net-like structure 23 or are to a large extent encompassed by them. In relation to the surface 12 of the intermediary pieces 21, 22, the shape deviations 19, 20 have different depths 24, 25, wherein these depths 24, 25 also change over the area of the shape deviations 19, 20 and can possibly reach down to the carrier layer 3, as shown for example in the shape deviation 19. The depth 24 of this shape deviation 19 thus corresponds to the overall thickness of the slip coating 9, which can be between 2 and 80 $\mu$m, preferably between 2 and 30 $\mu$m.

In addition, spacings 15, 16 between the individual shape deviations 19, 20 vary widely. Consequently, the ratio of the average spacings 15, 16 between the individual shape deviations 19, 20 to their depths 24, 25 in relation to the raised, net-like structure 23 or the intermediary pieces 21, 22 lies between 500:1 and 5:1. The average roughness depth, for example, lies between 0.5 and 100 $\mu$m, preferably between 1 and 40 $\mu$m.

As is furthermore schematically visible in the depiction in FIG. 1, 50 to 90%, preferably 60 to 80% of the partial area or of the section 7 is disposed as recessed by means of shape deviations 19, 20. Preferably, at least 50% of the shape deviations 19, 20 in the top view of the slip coating 9 are encompassed on all sides by the net-like structure 23, in particular by the intermediary pieces 21, 22.

Furthermore, in a preferable manner, an average roughness depth of the slip coating 9 or of the partial area of the section 7 lies between 0.5 and 100 $\mu$m, preferably between 1 and 40 $\mu$m. This average roughness depth represents the mathematical average of individual roughness depths, which are determined in five adjoining individual measured sections of equal length, as is explained in more detail below in conjunction with the exemplary embodiment in FIG. 2. What is achieved as a result is that a quite uniform adhesion potential or slip potential is achieved between the individual regions of the surface 12 or, in the event that the underside 11 is coated with a slip coating 9, on the surface connected with it, by means of which the slipperiness of the article 1 and primarily also the wet slipperiness can be considerably improved.

This differs from the processes of the prior art in that the product properties according to the invention are predominantly achieved via the roughness of the surface 12 or the underside 11, wherein with increasing average roughness depth of up to approx. 40 $\mu$m, the slipperiness in relation to human skin increases and the stickiness of the polymer surfaces decreases.

If the surface 12 or the underside 11, which constitutes the outer surface of the glove 4 is further roughened, in most products, a subjectively uncomfortable abrasive feel gradually increases as a function of hardness and modulus of elasticity. With roughness depths of over 100 $\mu$m, a significant increase in the polymer-polymer friction usually occurs and when there is abrasive contact with human skin, possibly leads to mechanically caused irritations. The surface properties described here with regard to their dependency on the average roughness depth are naturally also dependent on the type of roughness and the type of manufacturing used to produce it, as well as the polymer type and product type and have to be individually optimized for each polymer type and product type. It is advantageous that individual irritation zones in the sections 7, 18 that can negatively influence the positive overall effect of the embodiment according to the invention are fundamentally prevented by the average roughness depth, which is uniform over the sections 7 and 8, respectively.

In contrast to the surface roughnesses according to the invention, favorable slipperiness in relation to human skin can furthermore also be achieved with relatively soft polymers (e.g. polyacrylates), whereas with conventionally smooth slip coatings having the same polymers, there is no slipperiness in relation to skin. Because of the fact that softer polymers having higher tensile elasticities can be used in the surface layers according to the invention, with thin-walled articles 1 having high elasticity, the adhesion problems of the surface layer are reduced when the layer is stretched. Furthermore, the selection of the slip coating polymer is made significantly easier since the main influence factor for wearing comfort and slipperiness according to the invention is determined by the surface morphology.

Figure 2:
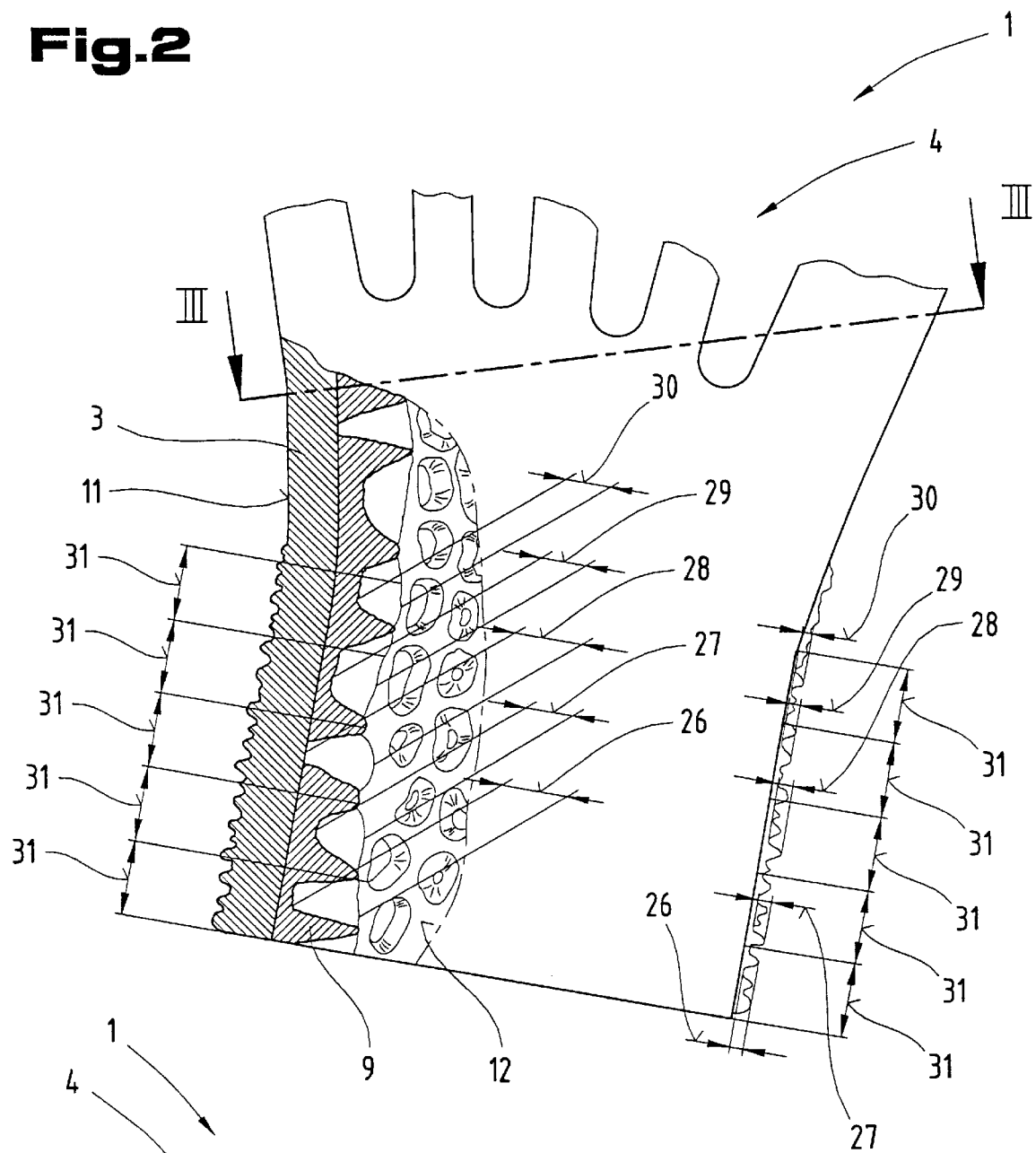
FIG. 2 is a partial section through a top view of an article according to the invention, in the form of a glove.
Figure 3:
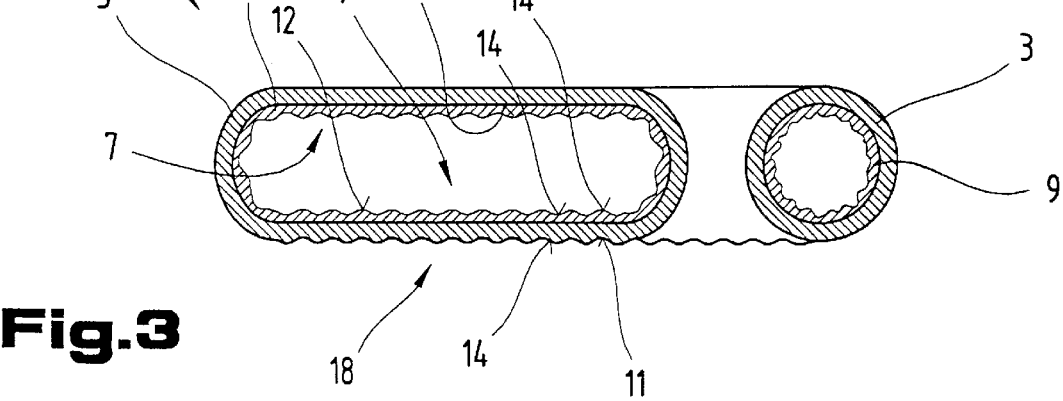
FIG. 3 is a simplified schematic representation of an end view of the article according to FIG. 2, cut along line III—III in FIG. 2.

The embodiment of an article 1 in the form of a powder-free glove 4, e.g. a medical glove, is represented in the variant in FIGS. 2 and 3.

The glove 4 depicted in FIGS. 2 and 3 is shown in the position it assumes when removed from the dipping form 6, wherein the surface 12, which is oriented toward the dipping bath side during production and receives the slip coating 9, constitutes the inside of the glove 4, while the underside 11 oriented toward the dipping form 6 during the production of the glove 4 constitutes the outside of the glove 4. Consequently, in the case of this glove 4, on the outer surface which the user of the glove 4 uses to grasp tools or components, there is a corresponding average roughness depth that lies between 0.5 and 100 $\mu$m, preferably between 1 and 40 $\mu$m, and is an image of the average roughness depth of the surface of the dipping form 6.

In order to produce the uniform morphology, as has also already been briefly explained by way of introduction, the dipping form 6 is used, which is usually slightly rough and is comprised of porcelain, and which has an average roughness depth between 0.5 and 100 $\mu$m, preferably 1 to 40 $\mu$m; it is dipped into an aqueous coagulation solution, which is comprised of e.g. calcium nitrate, polyethylene glycol, and a water soluble silicone type or chalk and is then dried for a short time with hot air. Then, for the depositing of the glove 4, the dipping form 6 is dipped into a for example pre-cross-linked natural latex mixture of which the carrier layer 3 is comprised.

The average roughness depth represents the mathematical average of individual roughness depths 26 to 30, which are determined in five adjoining individual measured sections of equal length 31. The average roughness depth in the region of the surface 13 thus represents a mirror image of the average roughness depth of the dipping form 6.

The average roughness depth on the surface 12 of the slip coating 9—which is deposited on the carrier layer 3 by means of the immersion of the dipping form 6 after a renewed short drying—is determined in the same manner by means of the individual roughness depths 26 to 30 in five adjoining individual measured sections of equal length 31.

However, the shape deviations 19 and 20 in this surface 12 are now either not influenced at all by the surface morphology of the dipping form 6 or are influenced by it to a reduced extent in accordance with the selected process, and are instead constituted by means of the manufacturing process during the production of the slip coating 9.

In the end view of the glove 4 in FIG. 3, it can be seen that the entire surface 12 that comprises the inside of the glove 4 is provided with corresponding shape deviations 19, 20 in accordance with the above description.

Moreover, for example, the underside 11 that comprises the outside of the glove 4 is provided with corresponding shape deviations 14, i.e. a roughening, only in the region that comes to rest over the inner surface of the hand, in order for example to improve grip security primarily when the gloves are used to grasp tools in the medical field or also in the assembly field. Naturally, it is also conversely possible to equip the entire underside 11, that is, the entire external surface of the glove 4, with corresponding shape deviations 14 and with a roughness comprised by means of this. The degree to which the section or a partial area of the section 18 is provided with shape deviations 14 or a roughening can be determined by the embodiment of the dipping form 6, in particular its surface roughness.

Figure 4:
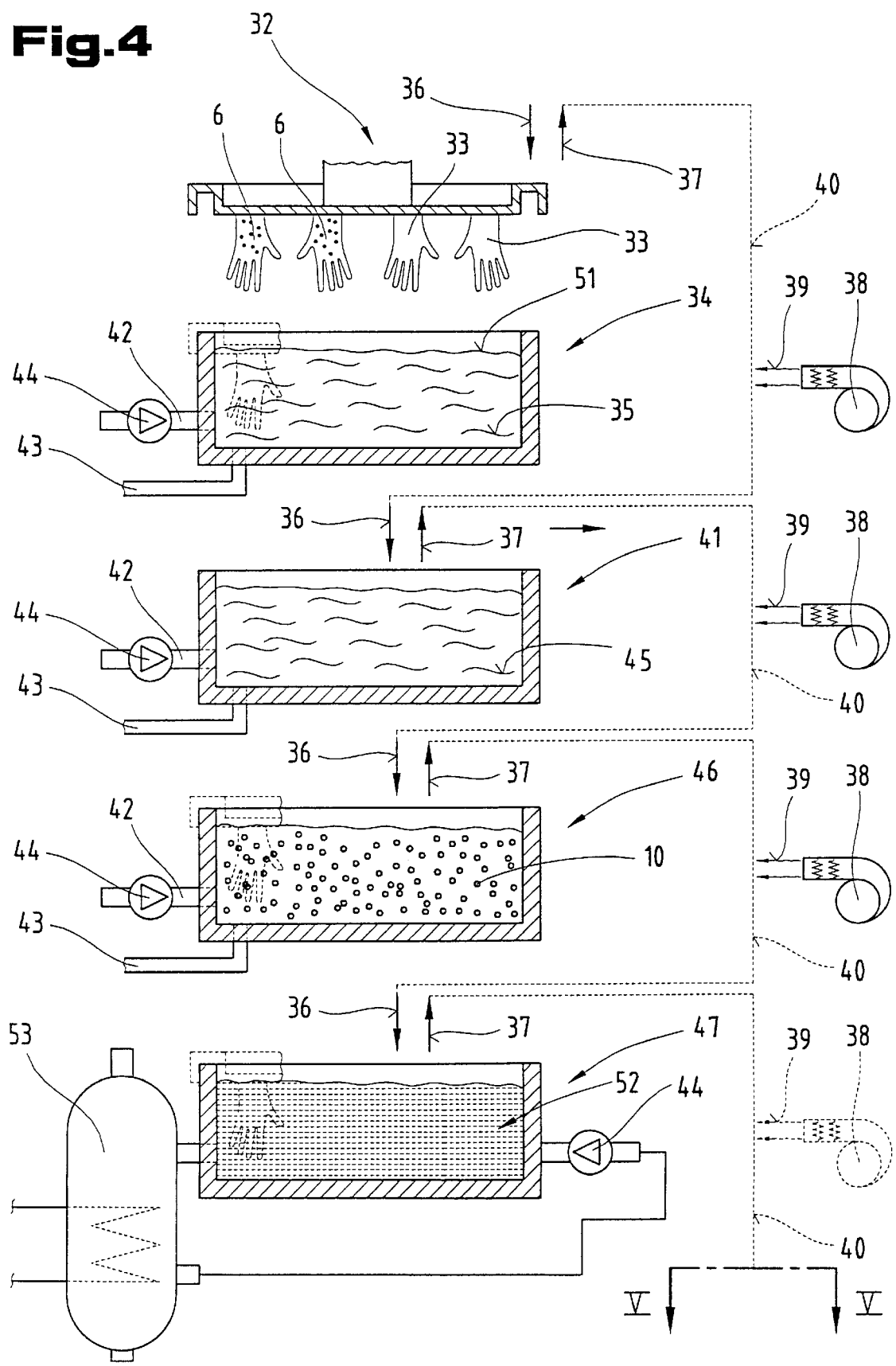
FIG. 4 is a simplified schematic representation of a part of the course of the process according to the invention for manufacturing an article.
Figure 5:
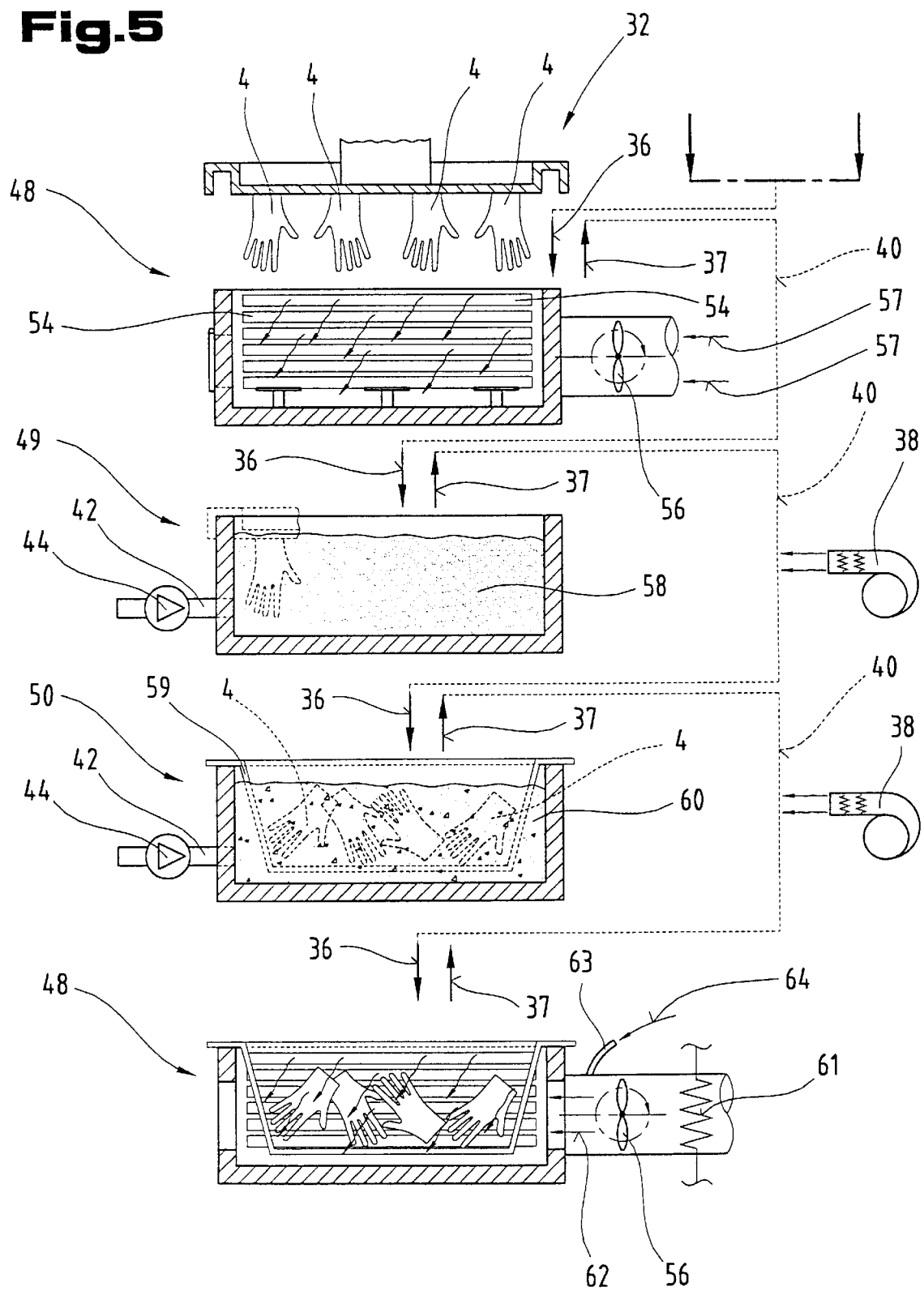
FIG. 5 is a simplified schematic representation of another part of the course of the process for manufacturing an article.

For the sake of increased clarity, this manufacturing process, which produces the average roughness depth shown schematically and completely out of proportion in the drawings in FIGS. 2 and 3, is explained in detail in conjunction with the schematically represented course of the process for manufacturing this kind of an article 1 or glove 4 by means of individual, successive apparatuses and apparatus parts represented in FIGS. 4 and 5.

To manufacture preferably powder-free gloves 4 out of a latex product 2, a number of dipping forms 6 are disposed on a form carrier 32 and are comprised, for example, of porcelain, plastic, metal, aluminum, or the like, with a surface 13 that has the desired shape deviations 14 in accordance with the above-indicated average roughness depth, while dipping forms 33 are disposed on the form carrier that have a smooth surface for the subsequent outside of a glove 4 to be manufactured out of latex.

The form carrier 32 is oriented toward a dipping basin in which an aqueous coagulation solution 35 is disposed. As has already been indicated by way of introduction, this can be comprised of calcium nitrate, polyethylene glycol and a water soluble silicone type or chalk. As indicated by the arrow 36, the form carrier 32 is dipped into the dipping basin 34, then removed from it in accordance with the arrow 37 and if need be, after an intermediary drying—as symbolically indicated by a hot air blower 38 and the arrows 39 that schematically represent the air heated for drying—are conveyed to another dipping basin 41 in accordance with the dotted lines 40.

Naturally, within the scope of this process according to the invention, it is left up to one skilled in the art as to whether the dipping of the dipping forms 6 or the form carrier 32 always takes place in the same dipping basin 34 and this basin is alternatingly filled with coagulation solution 35 or the latex product 45 or arbitrary other fluids or mediums via an inlet 42 and a discharge 43, e.g. via a schematically represented pump 44, or whether a number of dipping basins 34, 41, 46, 47, 48, 49, 50 are provided which are disposed in succession. It is also possible that the dipping of the dipping forms 6 is carried out by a relative movement of an arbitrary type between the form carrier 32 and the dipping basin 24, 41, and 46 to 50. Naturally, it is also possible that primarily the treatment steps or process steps in which the articles 1 or gloves 4 are already removed from the dipping forms 6, 33, are carried out in rotating containers, for example drums or the like, such as the ones used in conventional washing machines and driers, in order to move them during the treatment by means of constant rotation of the drum in order to also prevent the articles 1 or gloves 4 from sticking to each other during production.

Since all of these different possibilities for carrying out the process are known to one skilled in the art from the broad prior art, the depiction of the different devices for carrying out the individual steps of the process are eliminated and these are only explained in conjunction with the purely schematic representations in FIGS. 4 and 5.

After this intermediate drying of the coagulant or the coagulation solution 35 that is carried out if necessary, the dipping forms 6 are dipped into the dipping basin 41 so that the dipping forms 6 and 33 are dipped completely below a fluid level 51 of a latex product 45 of arbitrary composition, as previously indicated. The dipping forms 6 remain in the dipping basin 41 until a desired layer thickness of fluid latex product 45 can adhere to the surface of the dipping forms 6 or to the layer comprised of coagulation solution 35. To that end, it is also possible that the dipping forms 6, 33 are lifted out of the dipping basin 41 and dipped back into it several times.

Then, a short intermediary drying of the latex product 45 on the dipping forms 6, 33 is carried out in accordance with the dotted line 40, for example with hot air at the additional hot air blower 38, for which purpose the air can have a temperature from 70 to 140° C., preferably 90 to 110° C. and the dipping forms 6 can be exposed to this hot air for 15 to 60 sec. Preferably, the duration of hot air exposure and the temperature of the hot air are controlled so that on its surface, the layer of fluid latex product 45 passes from the liquid state into the gelatinous or solid state.

After that, the form carrier 32 with the dipping forms 6, 33, in accordance with the arrows 36, 37, is dipped into the dipping basin 46 in which a polymeric material 10 for producing the slip coating 9 is disposed. At this point, for the sake of clarity, it should be mentioned that it is naturally possible to adapt the viscosity of the polymeric material 10 or naturally also the viscosity of the latex product 45 or the coagulation solution 35 to the desired properties through the addition of one or more viscosity regulators which, to one skilled in the art, are known from the prior art in different embodiments. As a result, it is possible to adapt the viscosity of the products or materials, which are usually in the form of dispersions, to the desired employment purpose in order to achieve corresponding layer thicknesses when dipping or to achieve a uniform depositing of the various materials on a surface of the dipping forms 6, 33. For the sake of clarity, it should be mentioned at this point that in the current description, the term "latex" has been constantly used independently of whether it concerns a dispersion of this material, the hardened, dried, cross-linked layer, or the solid phase of this material, even if, for example in the case of natural latex, this substance is usually called caoutchouc. It would therefore also be possible to refer to the layers, which are comprised of the individual materials mentioned above, as caoutchouc layers. This polymeric material 10 can be composed in accordance with the preceding data.

After the form carrier 32 with the dipping forms 6, 33 is lifted out of the dispersion comprised of polymeric material to produce the slip coating 9, this additionally deposited slip coating 9, as schematically indicated, is dried with hot air, for example at a temperature between 70 and 140° C., preferably 90 to 110° C., for a period of 15 to 60 sec. Preferably, the temperature and the duration of the hot air treatment are modulated so that the surface of the slip coating 9 passes over into a gelatinous or solid state.

Immediately after this, the dipping forms 6, 33 with the raw parts of the articles 1 or gloves 4 disposed on them are dipped into another dipping basin 47 in which the slip coating 9 is sprayed or rinsed with hot water 52. To that end, the hot water 52 can be circulated through the dipping basin 47 by means of a pump 44 belonging to a heating furnace or a heat exchanger 53, by means of which the air is kept at a desired temperature between 40 and 95° C., preferably from 70 to 90° C.

The chemical reaction in the slip coating 9 and the carrier layer 3 is initiated or supported by means of this treatment with hot water 52 so that it leads to a beginning or to a complete coagulation in this layer.

After this hot water treatment, which can last from 15 sec. to 8 min., preferably 30 sec. to 4 min., the articles 1 or the gloves 4, in the position in which they are put on the dipping forms 6, 33, are removed from the dipping basin 47 so that the remaining water 52 can drain off.

FIG. 5 shows the continuation of the course of the process in accordance with the line V—V in FIG. 4. The gloves 4 removed from the water 52 are left in the open for a period of 10 to 180 sec., preferably 20 to 50 sec., which time serves as a draining period, or are dried by hot air, before they are acted upon by means of an infrared radiation in the dipping basin, in this instance a warming cabinet or heating furnace, so that the carrier layer 3 and the slip coating 9 are permanently fixed. The radiation surfaces 54 for the infrared radiation, which are preferably embodied as stove tiles, have a temperature between 350 and 700° C., and the articles 1 or gloves 4 are exposed to infrared radiation indicated schematically by the arrows 55 for a period of time between 1 and 5 min. To this end, it is necessary that by means of the dipping basin 48 or a corresponding drying device, the ambient air, in accordance with the schematically indicated arrows 57, can be blown through the heating chamber or the dryer or the dipping basin 48 by means of a ventilator 56.

After the drying of the articles 1 or the gloves 4, the dipping forms 6, 33, as shown in FIG. 5, are dipped with their form carriers 32 into the dipping basin 49, in which a parting compound 58, for example a powder such as talcum, chalk or cornstarch powder, or a silicon emulsion is disposed which, when the articles 1 or the gloves 4 are subsequently removed from the dipping forms 6, 33, and are simultaneously turned inside-out, should prevent the surfaces 12 oriented toward the dipping basins 34, 41, and 46 to 48 from sticking together.

After being removed, the articles 1 or the raw pieces of the gloves 4 are placed, for example, in a transport basket 59, which can also be shaped like a grating or can be provided with through openings, and this transport basket 59 is placed in the dipping basin 50 in which a bleach 60 is disposed, whose composition is known from the prior art. For example, a 0.5% sodium hypochloride mixed with approx. 0.2% hydrochloric acid can be used.

After the treatment with the bleach 60, the articles 1 or the gloves 4 are washed at least once, preferably several times, though, with water or with fluids known from the prior art, in order to remove the residues of bleaches or acids from e.g. separate treatments with acids and bleaches.

When this washing process is finished, the articles 1 or the gloves are placed with the transport basket 59 into a dipping basin 48 or into a drying chamber, in which heating elements 61 can be disposed either in the drying chamber or in an air intake duct for the air drying, so that the drying is carried out by means of air, schematically represented by arrows 62, which can be conveyed through the interior of the drying chamber via the ventilator 56 or a blower.

Naturally, any other form of drying is also possible, for example by using drums or the like. When a drying chamber of this kind is used, it is preferably possible to blow a silicone emulsion into the air flow via an additional line 63 in accordance with the arrow 64 shown, in order, for example, to coat the surfaces that constitute the outside of the glove 4 and if need be, those that constitute its inside, with silicone near or at the end of the drying process. Naturally, however, it is also possible to deposit this silicone coating in particular sections of the slip zones or the surface 12 or 13 in a likewise known manner by means of the dipping process in emulsions or by means of spray application.

With the above-described process, the roughness according to the invention or the average roughness depth in the slip coating 9 is achieved by virtue of the fact that while the slip coating 9 is being acted upon by the hot water 52, or immediately thereafter, 40 to 70%, preferably 50 to 60% of the water content is removed from the slip coating 9. Due to the rapid removal of water, relatively high surface tensions are produced in the region of the slip coating 9 and this leads to a lowering or reduction of the thickness of the slip coating 9 shown in FIG. 1, which can be between 2 and 80 μm, preferably from 2 to 30 μm, and corresponds, for example, to the depth 24 in FIG. 1, at which the shape deviation 19 is so large that it extends over the entire thickness of the slip coating 9, i.e. down to the top side 8 of the carrier layer 3.

These regions with reduced wall thickness of the slip coating 9 comprise the shape deviations 19, 20, which are to a large extent encompassed by the net-like structure 23 or its intermediary pieces 21, 22. These raised intermediary pieces 21, 22 of the net-like structure 23 cause the article 1 or the glove 4 to lie against the surface of human skin only along the intermediary pieces, and on the one hand, the area of contact with the skin is significantly reduced and on the other hand, the slipperiness, in particular the wet slipperiness, is considerably increased as a result. At the same time, cavities are produced in this way, which can also absorb the sweat produced during work so that the wearing comfort of this kind of articles 1 or gloves 4 is also considerably improved.

This improved slip effect can be increased even further by additionally depositing a layer of silicone, for example by means of immersion into a silicone emulsion or by means of charging the drying air with a silicon emulsion.

If the articles 1 or gloves 4 are supplied in loose form to a bleaching process for bleaching the side remote from the dipping bath when the slip coating 9 is being deposited, which side then comprises the outside of the article 1 or glove 4, then as a result, the slipperiness of the article 1 or the glove 4 can be still further improved.

After the drying process has been carried out in the dipping basin 50, the gloves 4 are then sorted together into pairs and supplied to other processing procedures such as sterilization and packaging.

The roughness according to the invention, though, can also be increased by means of many other known processes.

The simplest method for roughening articles 1 in addition to the roughness depth required by manufacture is comprised in that the dipping form 6, 33 which is covered with the still-soft article 1 or the slip coating 9, is conveyed, for example, through a sandblasting chamber or through a fluidized bed with fine glass beads. Excess particles from the blasting process usually have to be completely removed in subsequent steps of the process.

Figure 6:
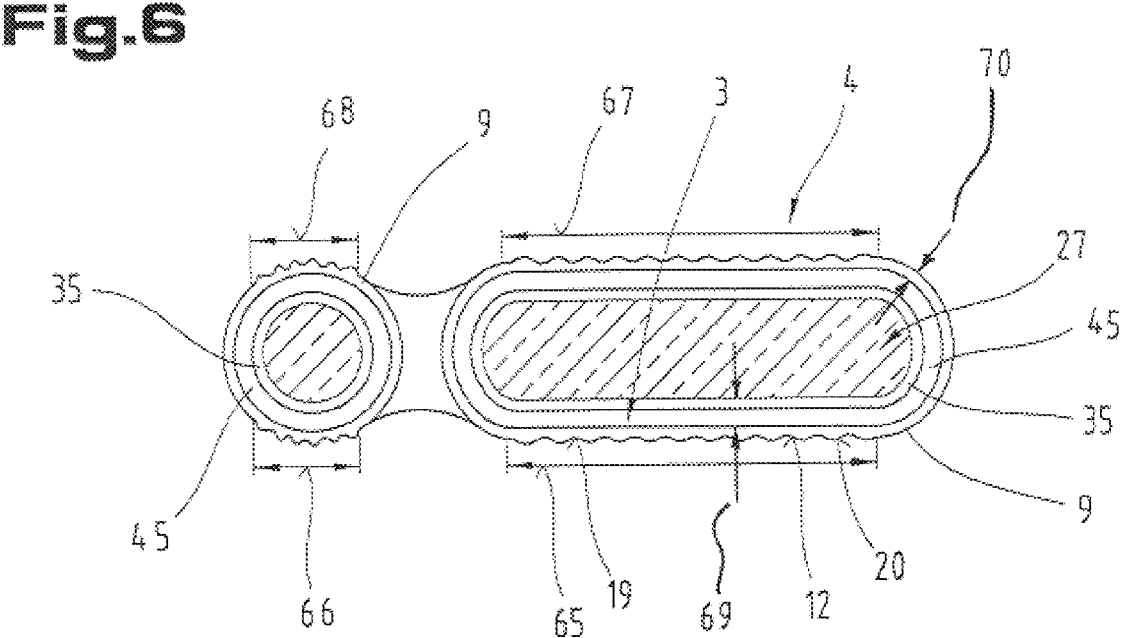
FIG. 6 is simplified schematic representation of a sectional end view of a porcelain form with the layers deposited on it for manufacturing an article according to the invention constituted by a glove.

Finally, in conjunction with a section through a glove 4 disposed on a dipping form 33, FIG. 6 shows that through the use of the dipping process, first a coagulation solution 35 is deposited on the surface that is for example embodied as smooth, followed by a latex product 45, whereupon the slip coating 9 is applied by dipping or spraying.

Through a corresponding embodiment of the devices for pressing the average roughness depth or the shape deviation 19, 20 into the surface 12, for example the above-mentioned glass beads or a corresponding pressing die can be used to produce additional roughening in the partial areas 65 to 68, before the manufacture of the above-described roughenings because of the shape deviations 19, 20.

For example, these partial areas extend only over a part of the horizontal faces of the article 1 that rest against the hand of the user. As a result, a sufficient wet slipperiness is achieved without the entire article being too severely weakened since in many cases, a high degree of slipperiness only has to be produced on those surfaces acted upon by an initial tension for the purpose of firmly seating the article 1 on a body part of the user. Within the scope of the invention, it is naturally also possible that by means of corresponding arrangements, for example the partial depositing of parting compounds or the like before the slip coating 9 is deposited, the slip coating 9 or at least the shape deviations 19, 20 are also produced on only one partial area or on individual partial areas 65 to 68.

Furthermore, the depiction in FIG. 6 shows that the carrier layer 3, which is comprised of the coagulation solution 35 and the latex product 45, can have a thickness 69 of 100 $\mu$m to 300 $\mu$m.

In contrast, the slip coating 9 disposed on this carrier layer 3 has, for example, a thickness 70 of 2 $\mu$m to 80 $\mu$m, preferably 2 $\mu$m to 30 $\mu$m.

Figure 7:
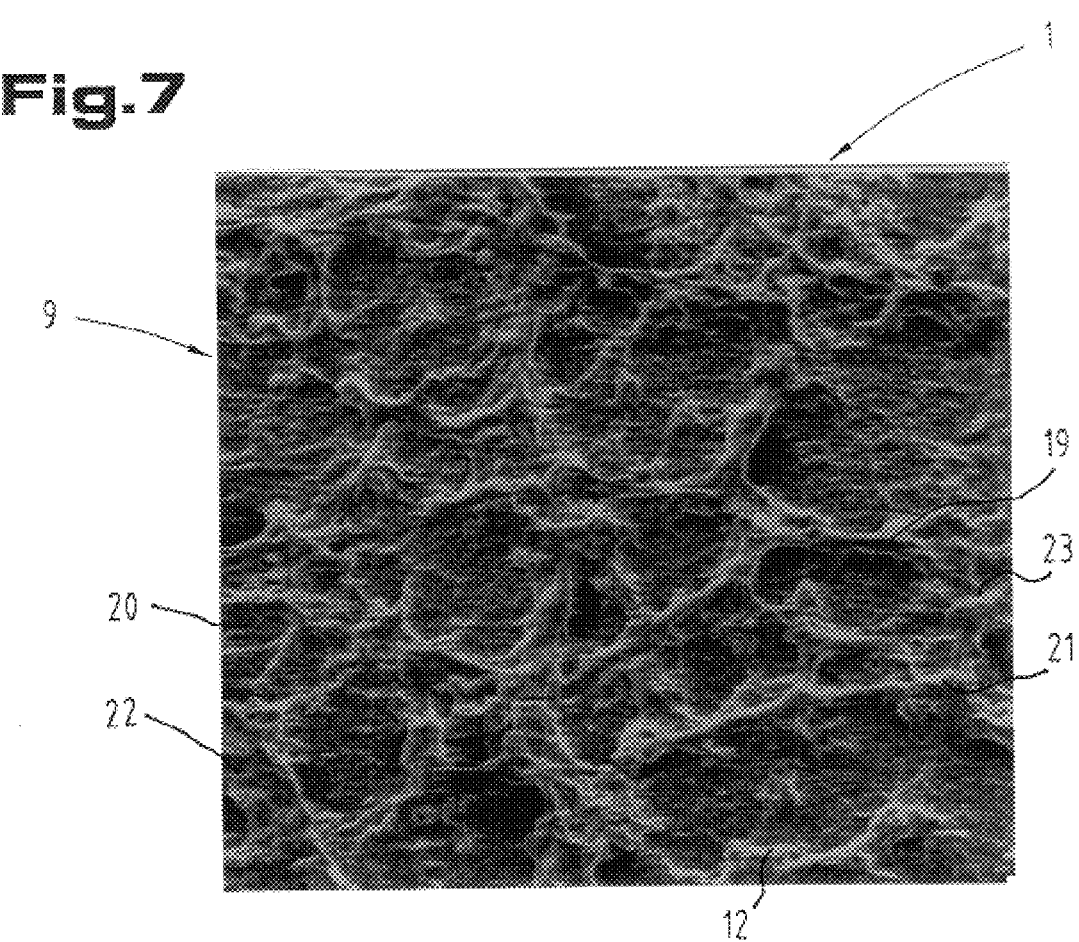
FIG. 7 is a top view of the surface of the slip coating of an article according to the invention, in a depiction that has been considerably enlarged by an electron microscope.

FIG. 7 shows a top view of a part of the surface 12 of the slip coating 9 of an article 1. This depiction very clearly shows the net-like structure 23, which is comprised by means of the intermediate pieces 21, 22 and encompasses the shape deviations 19, 20.

This depiction is a 100-fold enlargement of the surface 12 of the slip coating 9, produced by an electron microscope.

The variants described in the preceding figures as to choice of material for the carrier layer 3 and the slip coatings 9 can be used interchangeably. Naturally, the individual exemplary embodiments described above, the variants shown in these exemplary embodiments, and different embodiments can each constitute independent inventive embodiments in and of themselves and can be arbitrarily combined with one another. Pimarily, the individual embodiments characterized in FIGS. 1–7 can constitute the subject of independent embodiments according to the invention.

The objects and embodiments according to the invention with regard to this can be inferred from the detailed descriptions of these figures.

For the sake of clarity, is should be emphasized that for improved comprehension of the invention, the individual exemplary embodiments have been represented in a form that is partially distorted in scale or have been shown in enlarged fashion. Individual features of the combinations of features shown in the individual exemplary embodiments, all constitute embodiments according to the invention that are independent in and of themselves.

| Reference Numeral List |
| --- |
| 1 article |
| 2 latex product |
| 3 carrier layer |
| 4 glove |
| 5 polymer |
| 6 dipping form |
| 7 section |
| 8 top side |
| 9 slip coating |
| 10 material |
| 11 underside |
| 12 surface |
| 13 surface |
| 14 shape deviation |
| 15 space |
| 16 space |
| 17 depth |
| 18 section |
| 19 shape deviation |
| 20 shape deviation |
| 21 intermediary piece |
| 22 intermediary piece |
| 23 structure |
| 24 depth |
| 25 depth |
| 26 individual roughness depth |
| 27 ind. roughness depth |
| 28 ind. roughness depth |
| 29 ind. roughness depth |
| 30 ind. roughness depth |
| 31 length |
| 32 form carrier |
| 33 dipping form |
| 34 dipping basin |
| 35 coagulation solution |
| 36 arrow |
| 37 arrow |
| 38 hot air blower |
| 39 arrow |
| 40 line |
| 41 dipping basin |
| 42 inlet |
| 43 discharge |
| 44 pump |
| 45 latex product |
| 46 dipping basin |
| 47 dipping basin |
| 48 dipping basin |
| 49 dipping basin |
| 50 dipping basin |
| 51 fluid level |
| 52 water |
| 53 heat exchanger |
| 54 radiation surface |
| 55 arrow |
| 56 ventilator |
| 57 arrow |
| 58 parting compound |
| 59 transport basket |
| 60 bleach |
| 61 heating element |
| 62 arrow |
| 63 line |

-continued

Reference Numeral List 64 arrow
65 partial area
66 partial area
67 partial area
68 partial area
69 thickness
70 thickness

What is claimed is:

1. A flexible rubber or plastic article, comprising:
a surface;
a slip layer on at least a section of the surface, said slip layer comprising polymeric material fixed on and integrally formed with said surface, said polymeric material of the slip layer comprising at least one of natural latex and synthetic latex;
the slip layer including at least one partial area having a raised net-shaped structure and a plurality of recessed shape deviations having a spacing between adjacent shape deviations;
the plurality of recessed shape deviations having a roughness depth in relation to the. raised net-shaped structure; a
a ratio of the average spacings between adjacent shape deviations to their depth is between about 500:1 and about 5:1; and
the average roughness depth is between about 0.5 $\mu$m and about 100 $\mu$m.

2. The flexible article according to claim 1, wherein the average roughness depth is between about 1 $\mu$m and about 40 $\mu$m.

3. The flexible article according to claim 1, the partial area including a surface area, and the recessed shape deviations comprising between about 50% and about 90% of the surface area.

4. The flexible article according to claim 3, the recessed shape deviations comprising between about 60% and about 80% of the surface area.

5. The flexible article according to claim 1, wherein the raised net-shaped structure surrounds at least 50% of the shape deviations in a top view of the slip layer.

6. The flexible article according to claim 1, the polymeric material of the slip layer comprising a latex mixture.

7. The flexible article according to claim 1, the polymeric material of the slip layer comprising polyurethane.

8. The flexible article according to claim 1, the polymeric material of the slip layer comprising at least one member selected from the group consisting of polyacrylates, polymethacrylates and polysiloxanes.

9. The flexible article according to claim 1, the slip layer comprising 0 to 30 wt. % polyurethane, 1 to 40 wt. % polyacrylate, 1 to 20 wt. % polysiloxane and 0 to 40 wt. % filler.

10. The flexible article according to claim 9, the filler comprising at least one member selected from the group consisting of pulverized or powdered chalk, lime, cornstarch, silicon dioxide and gypsum.

11. The flexible article according to claim 1, the polymeric material of the slip layer comprising water absorbing groups.

12. The flexible article according to claim 1, the polymeric material of the slip layer comprising intensely hydrophilic groups.

13. The flexible article according to claim 12, the hydrophilic groups comprise at least one member selected from the group consisting of acrylic acid, methacrylic acid, acrylate and methacrylate.

14. The flexible article according to claim 1, wherein the polymeric material of the slip layer has high surface adhesion.

15. The flexible article according to claim 14, wherein the polymeric material of the slip layer is not cross-linked.

16. The flexible article according to claim 1, the slip layer comprising roughened regions that include silicone deposits.

17. The flexible article according to claim 1, the slip layer comprising silicone deposits.

18. The flexible article according to claim 17, wherein the silicone deposits comprise an amount between about 0.05 g/m$^2$ and about 3 g/m$^2$ on the at least a section of the surface.

19. The flexible article according to claim 18, wherein the silicone deposits comprise an amount of about 0.25 g/m$^2$ on the at least a section of the surface.

20. The flexible article according to claim 1, further comprising:
a sleeve-shaped carrier layer;
the sleeve-shaped carrier layer including an inner surface; and
the inner surface of the carrier layer including the slip layer.

21. The flexible article according to claim 1, further comprising:
a sleeve-shaped carrier layer;
the sleeve-shaped carrier layer including an outer surface; and
the outer surface of the carrier layer including the slip layer.

22. The flexible article according to claim 1, further comprising a plurality of sections having lower relative movement between the surface of the article and a user's skin, wherein the average roughness depth between the recessed shape deviations and the raised net-shaped structure is lower in the plurality of sections having lower relative movement.

23. The flexible article according to claim 1, further comprising:
a carrier layer;
the carrier layer including at least one layer;
the at least one layer including a polymer; and
the polymer including at least one of natural latex and synthetic latex.

24. The flexible article according to claim 23, further comprising:
the polymer of the at least one layer being slightly cross-linked; and
the slip layer being disposed on the carrier layer.

25. The flexible article according to claim 23, comprising the polymer of the at least one layer being pre-cross-linked.

26. The flexible article according to claim 1; comprising:
a carrier layer;
the carrier layer including an aqueous solution of a coagulant; and
the aqueous solution of a coagulant comprising at least one member selected from the group consisting of calcium nitrate, polyethylene glycol, a water soluble silicone or chalk, and a pre-cross-linked natural latex mixture.

27. The flexible article according to claim 1, further comprising:

a carrier layer; and the carrier layer including a pre-cross-linked synthetic latex.

28. The flexible article according to claim 27, the pre-cross-linked synthetic latex comprising at least one member selected from the group consisting of chloroprene latex, NBR latex, X-NBR latex and SBR latex.

29. The flexible article according to claim 1, further comprising:

a sleeve-shaped carrier layer; and the sleeve-shaped carrier layer including an inner surface and an outer surface.

30. The flexible article according to claim 1, further comprising:

the flexible article including an inner surface and an outer surface;

the inner surface of the article including the at least a section of the surface having the slip layer.

31. The flexible article according to claim 30, the flexible article comprising a glove.

32. The flexible article according to claim 1, further comprising:

an inner surface and an outer surface; and the outer surface of the flexible article including the at least a section of the surface having the slip layer.

33. The flexible article according to claim 32, the flexible article comprising a glove.

34. The flexible article according to claim 1, further comprising:

a carrier layer;

the carrier layer including a surface; and the surface of the carrier layer being chlorinated.

35. The flexible article according to claim 34, the chlorinated surface comprising a plurality of deformations composed of raised edge regions, wherein the plurality of raised edge regions protrude above a neighboring surface by a height of about 0.5 $\mu$m to about 10 $\mu$m.

36. The flexible article according to claim 35, wherein the raised edge regions protrude above the neighboring surface by a height of about 1 $\mu$m or less.

37. The flexible article according to claim 1, further comprising an inner surface, wherein the inner surface includes at least one of a coating of silicone and a treatment with chlorine.

38. The flexible article according to claim 1, the flexible article comprising a rubber glove.

39. The flexible article according to claim 38, the rubber glove comprising a medical glove.

40. The flexible article according to claim 1, the flexible article comprising a condom.

41. The flexible article according to claim 38, the rubber glove comprising an inner surface, and the inner surface including the slip layer.

42. The flexible article according to claim 41, the rubber glove comprising a medical glove.

43. The flexible article according to claim 41, further comprising:

the inner surface of the rubber glove including a region oriented toward a palm of a hand and a region oriented toward a back of the hand;

the region oriented toward the palm of the hand including the slip layer; and the region oriented toward the back of the hand including the slip layer.

44. The flexible article according to claim 42, further comprising:

the inner surface of the medical glove including a region oriented toward a palm of a hand and a region oriented toward a back of the hand;

the region oriented toward the palm of the hand including the slip layer; and the region oriented toward the back of the hand including the slip layer.

45. The flexible article according to claim 30, further comprising:

the outer surface including a plurality of shape deviations having a spacing between adjacent shape deviations;

the plurality of shape deviations having a depth in relation to the outer surface;

a ratio of the spacings between adjacent shape deviations to their depth is between about 100:1 and about 5:1; and an average roughness depth is between about 0.5 $\mu$m and about 100 $\mu$m.

46. The flexible article according to claim 45, wherein the average roughness depth is between about 1 $\mu$m and about 40 $\mu$m.

\* \* \* \* \*